United States Patent
Toyoshima et al.

(10) Patent No.: US 7,712,375 B2
(45) Date of Patent: May 11, 2010

(54) STRENGTH MEASURING METHOD OF HONEYCOMB STRUCTURE HAVING INSERTION HOLE

(75) Inventors: Hideyuki Toyoshima, Nagoya (JP); Takahiro Kondo, Nagoya (JP)

(73) Assignee: NGK Insulators, Ltd., Nagoya (JP)

(*) Notice: Subject to any disclaimer, the term of this patent is extended or adjusted under 35 U.S.C. 154(b) by 0 days.

(21) Appl. No.: 12/357,103

(22) Filed: Jan. 21, 2009

(65) Prior Publication Data

US 2009/0188326 A1    Jul. 30, 2009

(30) Foreign Application Priority Data

Jan. 30, 2008    (JP)    ............................. 2008-019432

(51) Int. Cl.
  *G01N 19/08*    (2006.01)
  *G01N 3/08*    (2006.01)
(52) U.S. Cl. .......................................... 73/799; 73/821
(58) Field of Classification Search .................. 73/799, 73/816, 821
See application file for complete search history.

(56) References Cited

U.S. PATENT DOCUMENTS

| | | | | |
|---|---|---|---|---|
| 3,906,782 A | * | 9/1975 | Early et al. | .................... 73/816 |
| 5,766,393 A | * | 6/1998 | Nishimura et al. | ........ 156/89.22 |
| 6,840,083 B2 | * | 1/2005 | Hijikata | ..................... 73/12.01 |
| 2004/0074094 A1 | | 4/2004 | Bruck | |
| 2007/0269634 A1 | * | 11/2007 | Suenobu et al. | ............. 428/116 |
| 2008/0114468 A1 | * | 5/2008 | Kumar | ..................... 623/23.56 |

FOREIGN PATENT DOCUMENTS

JP    A-2004-526564    9/2004

* cited by examiner

*Primary Examiner*—Lisa M Caputo
*Assistant Examiner*—Jonathan Dunlap
(74) *Attorney, Agent, or Firm*—Oliff & Berridge, PLC

(57) ABSTRACT

There is disclosed a method for measuring the strength of a honeycomb structure provided with an insertion hole preferably without generating any chipping. In the strength measuring method of the honeycomb structure, the strength is measured while a rubber plug is inserted into the insertion hole. The rubber plug has a hardness of 45 or more and 90 or less, a clearance between the inserted rubber plug and the inner surface of the insertion hole parallel to the depth direction of the insertion hole is 0.2 mm or more and 2.6 mm or less, and the protruding height of the inserted rubber plug from the peripheral surface of the honeycomb structure is 0.5 mm or more and 5 mm or less.

16 Claims, 5 Drawing Sheets

STRENGTH MEASURING METHOD OF HONEYCOMB STRUCTURE HAVING INSERTION HOLE

BACKGROUND OF THE INVENTION

1. Field of the Invention

The present invention relates to a method for measuring the strength of a honeycomb structure provided with a hole into which, for example, a sensor is inserted.

2. Description of the Related Art

To prevent environmental pollution and improve the environment, a catalyst converter is used for the treatment of an exhaust gas from a car. This catalyst converter converts harmful substances (nitrogen oxide, carbon monoxide, etc.) included in the exhaust gas into components which can be discharged to the environment in accordance with law's provisions. When the exhaust gas passes through the catalyst converter, the harmful substances included in the gas are decreased.

However, in a case where it is confirmed whether or not the harmful substances have actually been decreased, it is difficult to directly measure the concentration of the harmful substances in the exhaust gas by use of a sensor.

To solve the problem, the function of the catalyst converter is monitored instead. When the catalyst converter functions, the harmful substances must be decreased. To monitor the function of the catalyst converter, there is employed means for arranging oxygen sensors, for example, back and forth of the catalyst converter, respectively, and measuring the content of oxygen in the exhaust gas by use of these sensors to speculate the accumulation capacity of a catalyst and the progress of an aging process. Alternatively, there is employed means for arranging heat sensors back and forth of the catalyst converter, respectively, and measuring the temperature change of the exhaust gas by use of these sensors to speculate whether or not the catalyst converter works (e.g., see JP-T-2004-526564).

When the above sensors are inserted into holes formed in a honeycomb structure similar to a carrier of the catalyst converter of the catalyst converter and installed together with the honeycomb structure in an exhaust system of the car, the exposure of the sensors to oil, fuel, condensate water and the like encountered in the exhaust system can be prevented, and the stability of the sensors for a long period can be secured. Moreover, heat is usually taken by vaporization of the condensate water to disturb the early heating of the sensors. However, when the sensors are disposed in the honeycomb structure, rapid heating by a sensor heater at an early stage can be performed, and λ-control at the early stage immediately after starting an engine is realized to obtain an emission decreasing effect. In addition, restriction on a space is eased.

It is to be noted that as a prior document suggested to solve the same theme as that of the present invention described later or a similar theme, for example, JP-T-2004-526564 can be exemplified.

Additionally, even in the honeycomb structure provided with the holes into which the sensors are inserted, a constant strength is demanded in the same manner as in a filter or the catalyst carrier. When the honeycomb structure is broken, a sensor function might be lost, and a detection accuracy might lower.

However, when the strength of the honeycomb structure provided with the holes is measured by an isostatic breakdown strength test, there are confronted problems that hole edge portions are cracked by urethane wrapping the honeycomb structure therein or urethane is broken and that the strength of the honeycomb structure cannot be measured.

SUMMARY OF THE INVENTION

The present invention has been developed in view of such a situation, and an object thereof is to provide a method for measuring the strength of a honeycomb structure provided with a hole into which, for example, a sensor is inserted preferably without generating any crack in a hole edge portion. As a result of repeated investigations, it has been found that the above problem can be solved by the following means.

That is, according to the present invention, there is provided a strength measuring method of a honeycomb structure provided with an insertion hole, in which the strength of the honeycomb structure is measured while a rubber plug satisfying the following conditions (1) to (3) is inserted into the insertion hole:

(1) the rubber plug has a hardness of 45 or more and 90 or less;

(2) a clearance between the inserted rubber plug and the inner surface of the insertion hole parallel to the depth direction of the insertion hole is 0.2 mm or more and 2.6 mm or less; and (3) the protruding height of the inserted rubber plug from the outer surface of the honeycomb structure is 0.5 mm or more and 5 mm or less.

In the strength measuring method of the honeycomb structure according to the present invention, the rubber plug preferably further satisfies the following condition (4):

(4) the rubber plug has a recessed portion in the face thereof facing the inner surface of the insertion hole (parallel to the depth direction of the insertion hole).

In the strength measuring method of the honeycomb structure according to the present invention, the bottom of the insertion hole preferably has a semispherical shape.

In the strength measuring method of the honeycomb structure according to the present invention, the honeycomb structure as a measuring target may have any shape (profile), but preferably has the shape of a straight post including a circular or elliptic section vertical to a central axis, and the peripheral surface of the honeycomb structure having the straight post shape is preferably provided with the insertion hole. In this case, the peripheral surface of the honeycomb structure is the outer surface thereof, and the protruding height of the rubber plug from the outer surface of the honeycomb structure according to the above (3) is defined as the protruding height from the peripheral surface.

The strength measuring method of the honeycomb structure according to the present invention is preferably usable in a case where the above strength is (a strength) measured by an isostatic breakdown strength test defined by Automobile Standard JASO Standard M505-87 issued by Society of Automotive Engineers of Japan.

As described above, in the strength measuring method of the honeycomb structure according to the present invention, the target of the method is preferably the honeycomb structure having the shape of the straight post including the circular or elliptic section vertical to the central axis. This is a structure having an outer shape constituted of two circular or elliptic end faces and a peripheral surface connecting these end faces to each other, that is, a columnar shape or an elliptic post shape. A line connecting the centers of the circular or elliptic shapes constituting the two end faces is the central axis. The insertion hole is, for example, a hole (a space) formed in the peripheral surface of this honeycomb structure and directed to the central axis. A sensor or the like is inserted into the hole, and hence the hole is referred to as the insertion hole. The insertion hole may or may not be directed from the peripheral surface to the central axis. Moreover, the insertion hole may or may not have a direction parallel to the two end faces. That is, in a section crossing the central axis and extending through the insertion hole, the insertion hole may be formed to tilt from the peripheral surface to the one end face. In other words, when the honeycomb structure is raised with one end face being the bottom surface, the insertion hole opened in the peripheral surface (a side surface) may be directed, for example, downwards.

In the strength measuring method of the honeycomb structure according to the present invention, the rubber plug is a formed article made of a rubber. Since this article is inserted into the insertion hole during strength measuring, the article is referred to as the plug. The hardness of the rubber plug (the rubber) described in the above (1) is a type A durometer hardness (hardness HA) measured in conformity to Japanese Industrial Standards (JIS) K6253.

The inner surface of the insertion hole parallel to the depth direction of the insertion hole as described in the above (2) is a face which can come in contact with the rubber plug when the rubber plug is inserted, among faces forming the insertion hole (the space) opened in the outer surface of the honeycomb structure. The depth direction of the insertion hole corresponds to an inserting direction, and hence the inner surface of the insertion hole parallel to the depth direction of the insertion hole corresponds to a face parallel to the inserting direction. The inner surface of the insertion hole parallel to the depth direction of the insertion hole corresponds to the peripheral surface (the side surface) of the columnar portion, when, for example, the insertion hole (the space) has such a shape that the only bottom surface thereof is hemispherical and that another portion thereof is substantially columnar. The clearance is a distance between the surface of the rubber plug and the inner surface of the insertion hole. Since there is a clearance between the inserted rubber plug and the insertion hole, the insertion hole is larger that the rubber plug, and the plug can easily be inserted.

The protruding height of the inserted rubber plug from the outer surface of the honeycomb structure described in the above (3) is the maximum height of the rubber plug (completely) inserted into the insertion hole and protruding from the outer surface (e.g., the peripheral surface) of the honeycomb structure. In other words, when the strength measuring method of the honeycomb structure according to the present invention is performed, the inserted rubber plug is not fit in (apparently assimilate into) with the outer surface of the honeycomb structure, and slightly protrudes from the outer surface.

The face (of the rubber plug) facing the inner surface of the insertion hole described in the above (4) is a face which can come in contact with the face forming the insertion hole when the rubber plug is inserted. As described above, the inner surface of the insertion hole parallel to the depth direction of the insertion hole corresponds to the face parallel to the inserting direction, and hence the face of the rubber plug facing the inner surface of the insertion hole is also the face parallel to the inserting direction. Moreover, in a case where the rubber plug has such a shape that, for example, the only bottom surface thereof is hemispherical and that another portion thereof is substantially columnar, the face corresponds to the peripheral surface (the side surface) of the columnar portion. The recessed portion is a concaved space or dent. When the rubber plug substantially has the columnar shape, the recessed portion is preferably circumferentially provided in the peripheral surface of the rubber plug. Moreover, the recessed portion of the inserted rubber plug is preferably provided in the vicinity of the opening of the insertion hole opened in the outer surface of the honeycomb structure on conditions that the portion does not protrude from the insertion hole.

In the strength measuring method of the honeycomb structure according to the present invention, the strength of the honeycomb structure is measured while inserting, into the insertion hole, the rubber plug satisfying the conditions that (1) the rubber plug has a hardness of 45 or more and 90 or less; (2) the clearance between the inserted rubber plug and the inner surface of the insertion hole parallel to the depth direction of the insertion hole is 0.2 mm or more and 2.6 mm or less; and (3) the protruding height of the inserted rubber plug from the outer surface of the honeycomb structure is 0.5 mm or more and 5 mm or less. Therefore, the mechanical strength of the honeycomb structure provided with the insertion hole can be measured.

A mat of a portion corresponding to the insertion hole of the honeycomb structure is hollowed and canned, so that any load is not imposed onto the vicinity of the insertion hole of the honeycomb structure into which the sensor is inserted at a time when the structure is used. In the strength measuring method of the honeycomb structure according to the present invention, as described in (3), since the protruding portion of the inserted rubber plug is provided, the load around the insertion hole is decreased. When the isostatic breakdown strength test is performed, urethane can be prevented from biting into the insertion hole, and the strength can be measured in a state which closely resembles an actual use environment. Moreover, as described in (2), since the clearance is provided, the insertion hole is not reinforced, and the strength of the honeycomb structure provided with the insertion hole can be measured. According to the strength measuring method of the honeycomb structure of the present invention, it is possible to measure the lowering degree of the strength of the honeycomb structure provided with the insertion hole as compared with a honeycomb structure in which any insertion hole is not formed. Therefore, it can be judged whether or not the honeycomb structure has such a strength as to bear long-term use even against the load imposed during the canning or under a held pressure at a time when the sensor is installed in the insertion hole in an actual use configuration.

In a case where the strength measuring method of the honeycomb structure according to the present invention is not used, it cannot be judged whether or not the honeycomb structure has such a strength as to bear the long-term use even against the load imposed during the canning or under the held pressure at a time when the sensor is installed in the insertion hole in the actual use configuration. This causes a problem that it is unclear whether or not the structure has such a strength as to bear the long-term use. According to the present invention, such a problem can be avoided.

In a preferable configuration of the strength measuring method of the honeycomb structure according to the present invention, the rubber plug has the recessed portion in the face thereof facing the inner surface of the insertion hole, so that any chip is not generated in the vicinity of the insertion hole after the measuring. This is supposedly because an internal stress generated based on an external force exerted during the strength measuring is absorbed by deformation which does not lead to breakdown due to the presence of the recessed portion.

Figure 1A:
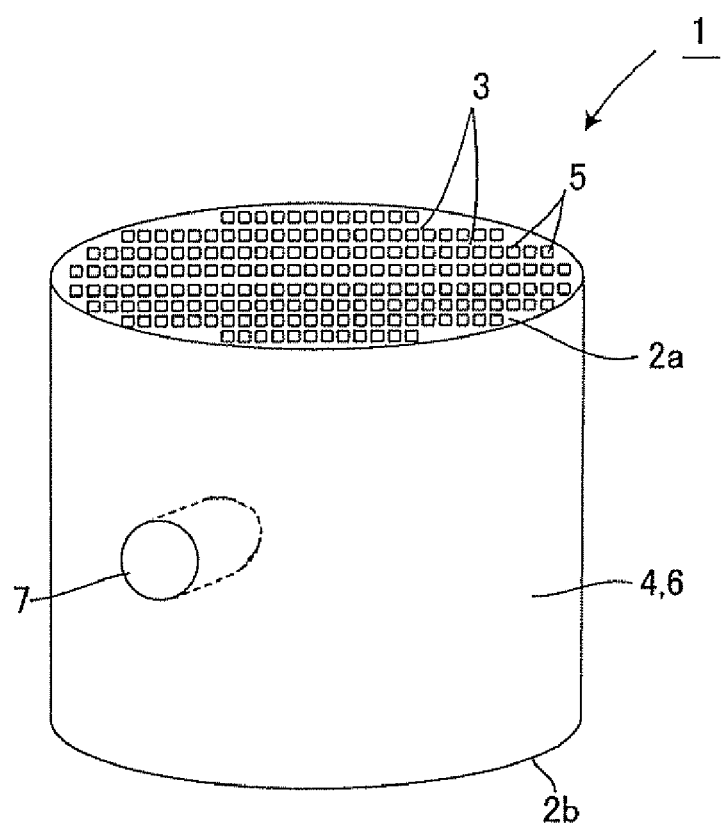
FIG. 1A is a perspective view showing one example of a honeycomb structure provided with an insertion hole, as a target of a strength measuring method of a honeycomb structure according to the present invention.

DESCRIPTION OF REFERENCE NUMERALS 1, 100: honeycomb structure
2a, 2b: end face
3: partition wall
4: outer wall
5: cell
6: peripheral surface
7: insertion hole
7a, 7b, 7c, 7d, 7e, 7f: insertion hole (the shape of respective one of the insertion holes, viewed from a certain direction)
8: rubber plug
8a, 8b, 8c, 8d: rubber plug

DESCRIPTION OF THE PREFERRED EMBODIMENT

Hereinafter, embodiments of the present invention will be described appropriately with reference to the drawings, but the present invention should not be limited to these embodiments when interpreted. The present invention can variously be altered, modified, improved or replaced based on the knowledge of any person skilled in the art without departing from the scope of the present invention. For example, the drawings show the preferable embodiments of the present invention, but the present invention is not limited to any configuration or information shown in the drawings. To implement or verify the present invention, means similar or equivalent to means described in the present specification can be applied, but preferable means is as follows.

First, a honeycomb structure provided with an insertion hole will be described as a target of a strength measuring method of the honeycomb structure according to the present invention.

Figure 1B:
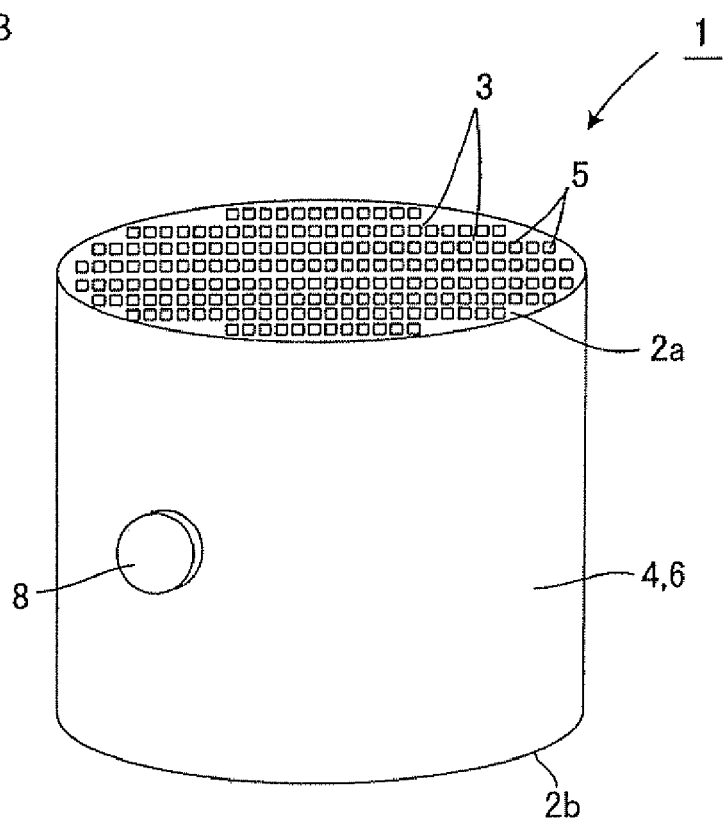
FIG. 1B is a perspective view showing that a rubber plug is inserted into the insertion hole of the honeycomb structure shown in FIG. 1A.

FIG. 1A is a perspective view showing one example of the honeycomb structure provided with the insertion hole, and FIG. 1B is a perspective view showing that a rubber plug is inserted into the insertion hole of the honeycomb structure. The outer shape of a honeycomb structure 1 shown in FIGS. 1A and 1B is a columnar shape constituted of two end faces 2a, 2b and a peripheral surface 6 which connects the end faces 2a and 2b to each other. In other words, the honeycomb structure 1 is a straight pole article having a circular section vertical to a central axis. The inside of the honeycomb structure 1 is constituted of porous partition walls 3 which separate and form a plurality of cells 5 constituting flow paths of a fluid flowing between the end faces 2a and 2b, and an outer wall 4 constituting the peripheral surface 6 is provided outside the partition walls 3. The peripheral surface 6 as the outer surface of the honeycomb structure 1 is provided with an insertion hole 7 which is directed to the central axis to extend through the cells 5, and a rubber plug 8 is inserted into the insertion hole 7.

Figure 2A:
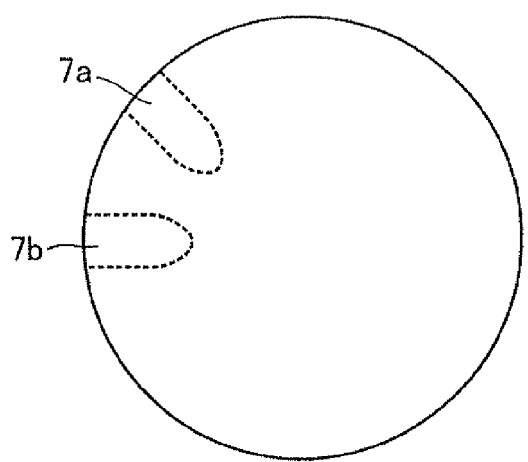
FIG. 2A is a plan view schematically showing the shape of the honeycomb structure as the target of the strength measuring method of the honeycomb structure according to the present invention and showing various configurations of the insertion hole formed in the structure.
Figure 2B:
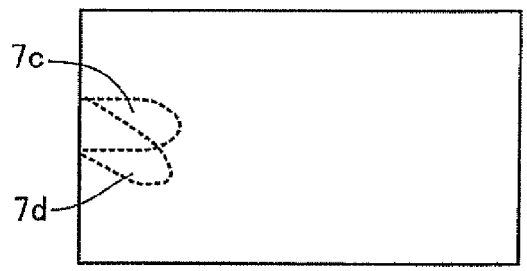
FIG. 2B is a front view schematically showing the shape of the honeycomb structure as the target of the strength measuring method of the honeycomb structure according to the present invention and showing various configurations of the insertion hole formed in the structure.
Figure 3A:
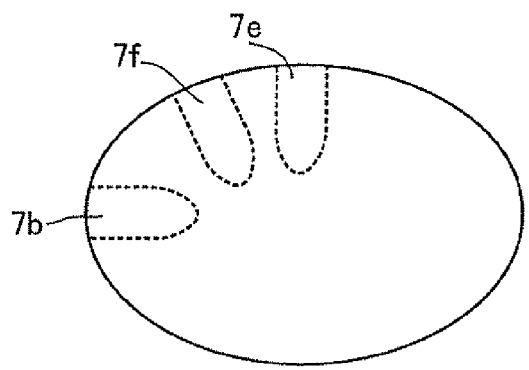
FIG. 3A is a plan view schematically showing the shape of the honeycomb structure as the target of the strength measuring method of the honeycomb structure according to the present invention and showing various configurations of the insertion hole formed in the structure.
Figure 3B:
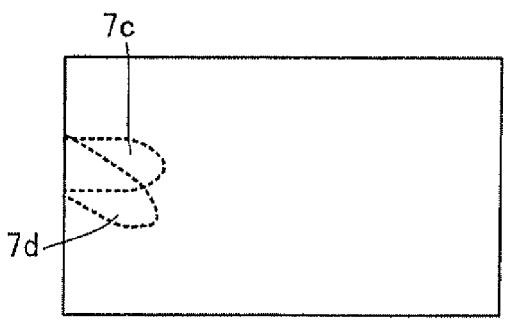
FIG. 3B is a front view schematically showing the shape of the honeycomb structure as the target of the strength measuring method of the honeycomb structure according to the present invention and showing various configurations of the insertion hole formed in the structure.

FIGS. 2A, 2B, 3A and 3B are schematic diagrams showing the shape of the honeycomb structure and various configurations of the insertion hole formed in the structure. FIGS. 2A and 23 are diagrams of a honeycomb structure having a columnar shape, FIG. 2A is a plan view (a view of an end face from the upside), and FIG. 2B is a front view (a view of a peripheral surface from the front side). FIGS. 3A and 3B are diagrams of a honeycomb structure having an elliptic post shape (a straight post article having an elliptic section vertical to the central axis), FIG. 3A is a plan view (a view of an end face from the upside), and FIG. 3B is a front view (a view of a peripheral surface from the front side). In FIGS. 2A, 2B, 3A and 3B, any cell or the like is not drawn, and an insertion hole is shown by a broken line in a perspective view.

As described above, FIGS. 2A, 2B, 3A and 3B are diagrams showing various configurations of the insertion hole formed in the honeycomb structure. For example, in the honeycomb structure having the columnar shape (see FIGS. 2A and 2B), the actual insertion hole is an insertion hole 7a (viewed from the upside) and an insertion hole 7c (viewed from the front side). Alternatively, for example, in the honeycomb structure having the elliptic post shape (see FIGS. 3A and 3B), the actual insertion hole is an insertion hole 7f (viewed from the upside), an insertion hole 7d (viewed from the front side) and the like. That is, examples of the configuration of the insertion hole of the honeycomb structure provided with the insertion hole as the target of the strength measuring method of the honeycomb structure according to the present invention include one of the insertion hole 7a and an insertion hole 7b which is one of the insertion holes 7c and 7d, and one of the insertion hole 7b, an insertion hole 7e and the insertion hole 7f which is one of the insertion holes 7c and 7d. In the present specification, for example, the insertion hole which is the insertion hole 7a and the insertion hole 7c, or the insertion hole shown by the insertion hole 7a and the insertion hole 7c indicates the configuration of the insertion hole.

The insertion hole (the depth direction of the insertion hole) may not be directed in parallel with two end faces as in the insertion hole 7d shown in FIGS. 2B and 3B, and may tilt (e.g.) downwards (e.g., as much as about 10 to 20° toward the end face 2b). Alternatively, the insertion hole may be directed in parallel with the two end faces as in the insertion hole 7c. Usually in the honeycomb structure, since the cells are formed in such a direction that two end faces are faced to connect each other, the insertion hole is directed vertically to the cells (in such a direction as to connect the end faces to each other) in the latter case. It is to be noted that one insertion hole is present in each honeycomb structure in many cases, but a plurality of insertion holes may be formed).

Figure 4:
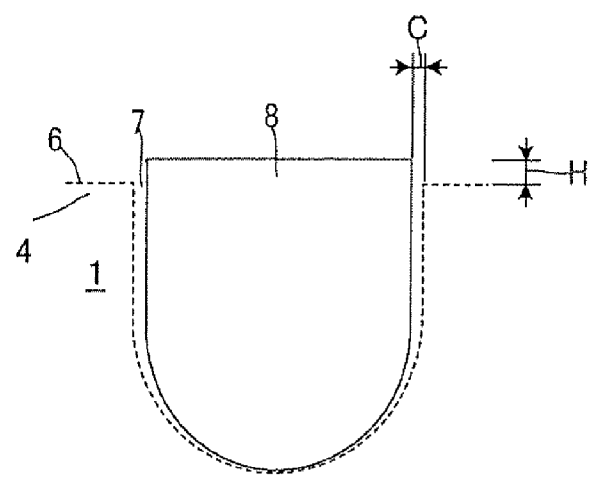
FIG. 4 is an enlarged sectional view showing one embodiment of the strength measuring method of the honeycomb structure according to the present invention and showing that a rubber plug is inserted into an insertion hole formed in the peripheral surface of the honeycomb structure.

FIG. 4 is an enlarged sectional view showing that a rubber plug is inserted into an insertion hole formed in the peripheral surface of the honeycomb structure. FIG. 4 is a diagram for explaining a clearance between (the face of) the inserted rubber plug and the inner surface of the insertion hole parallel to the depth direction of the insertion hole and the protruding height of the inserted rubber plug from the outer surface of the honeycomb structure as characteristics of the strength measuring method of the honeycomb structure according to the present invention. As described above, a clearance C is a distance between the surface of the rubber plug 8 and the inner surface of the insertion hole 7 (shown by a broken line), and a protruding height H is a height (the maximum height, if the height is not uniform) of a portion of the plug protruding from the outer surface of the honeycomb structure 1 (e.g., the peripheral surface 6 (shown by a broken line)).

There is not any restriction on the honeycomb structure provided with the insertion hole as the target of the strength measuring method of the honeycomb structure according to the present invention, but the thicknesses of the partition walls 3 are preferably about 10 to 1000 µm, the thickness of the outer wall 4 is preferably about 0.05 to 2 mm, a cell density is preferably amount 5 to 250 cells/cm$^2$, a diametric size (the length of a major axis in a case where the section vertical to the central axis has an elliptic shape) is preferably 40 to 300 mm, and the length of the central axis is preferably about 50 to 200 mm. Moreover, a material forming the partition walls 3 and the outer wall 4 is preferably a cordierite-containing material, and a porosity (a value measured by a mercury porosimeter) is preferably 10 to 90%.

EXAMPLES

Next, the present invention will specifically be described in accordance with examples. The present invention is not limited to these examples.

Example 1

[Preparation of Honeycomb Structure] As a raw material, a cordierite forming material including talc, kaolin and alumina as main materials is blended with water, a binder, a surfactant or the like, and the resultant mixed and kneaded forming material was extrusion-formed using a clay kneader and an extruder to obtain a formed honeycomb article having partition walls which separate and form a plurality of cells constituting fluid flow paths and an outer wall formed integrally with the partition walls. Then, the resultant formed honeycomb article was dried, then cut into predetermined lengths, and fired to obtain a honeycomb structure. As to the size and the shape of the resultant honeycomb structure, the structure had a columnar shape with a diameter of 118.4 mm and a total length (the length of the central axis) of 152.4 mm (see the shape shown in FIGS. 2A and 2B), the thicknesses of the partition walls were 0.15 mm (6 mil), a cell density was about 62 cells/cm$^2$ (400 cells/square inch) and a porosity was 35%.

Figure 5:
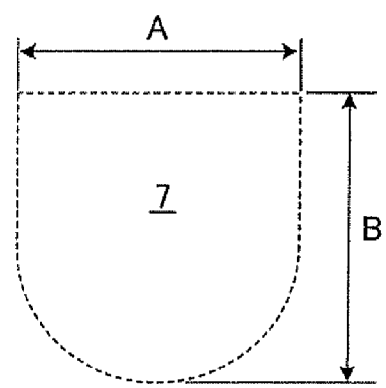
FIG. 5 is a diagram showing an insertion hole formed in a honeycomb structure in an example.

[Formation of Insertion Hole] In the center of the peripheral surface of the resultant honeycomb structure, an insertion hole (see the configuration shown by the insertion hole 7b of FIG. 2A and the insertion hole 7c of FIG. 2B) was directed to the central axis and formed in parallel with a section vertical to the central axis (in parallel with end faces) by using a machining center manufactured by Mori Seiki Co., Ltd. The insertion hole (a space) was formed into such a shape that the only bottom surface thereof was semispherical and that another portion thereof was substantially columnar. FIG. 5 is a diagram showing the shape of the formed insertion hole 7 by a broken line, and is a diagram showing the shape of the insertion hole 7 appearing in a section crossing the central axis of the honeycomb structure and extending along the center of the insertion hole. As to the size of the insertion hole 7, a diameter A of an opening opened in the peripheral surface of the honeycomb structure was 25 mm (a radius of 12.5 mm), and a depth B directed from the peripheral surface to the central axis was 21 mm (see FIG. 5).

Figure 6:
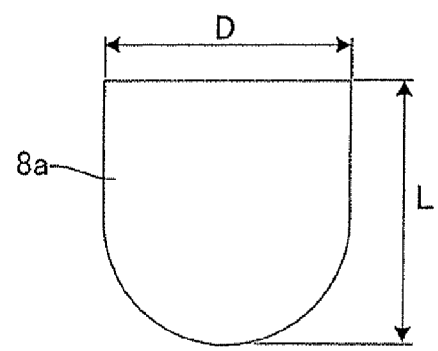
FIG. 6 is a sectional view showing the shape of a rubber plug used in the example and corresponding to a diagram of the insertion hole shown in FIG. 5.

[Insertion of Rubber Plug] A rubber plug having a hardness of 45 was inserted into the honeycomb structure provided with the insertion hole. FIG. 6 is a sectional view showing the shape of a used rubber plug 8a and corresponding to a diagram of the insertion hole 7 shown in FIG. 5. The shape of the used rubber plug 8a was substantially the same as that of the insertion hole 7, so that the only bottom surface thereof was semispherical and another portion was substantially columnar. As to the size of the rubber plug 8a, the diameter D of the columnar portion was set to 24.6 mm (a radius of 12.3 mm), and a clearance of 0.2 mm was provided between the plug and the inner surface of the insertion hole 7. Moreover, a length L of the inserted plug directed from the peripheral surface to the central axis was set to 21.5 mm, and the protruding height of the inserted plug from the peripheral surface was set to 0.5 mm.

Figure 11:
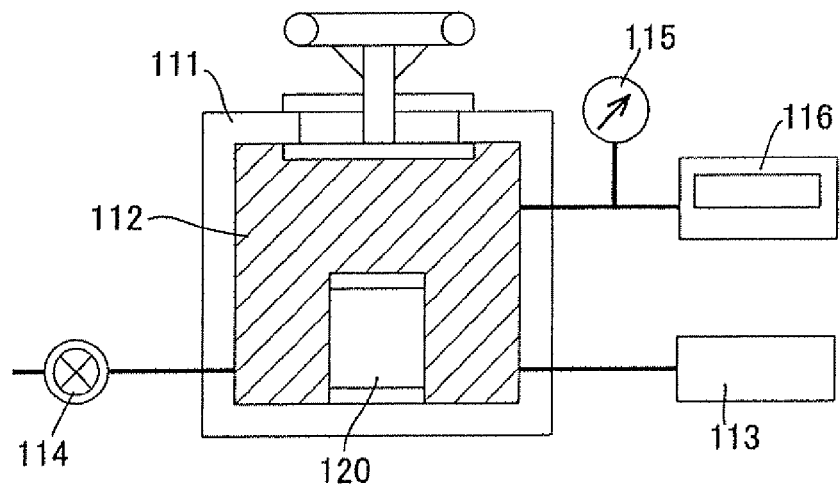
FIG. 11 is a schematic diagram showing a test device used in the example.
Figure 12:
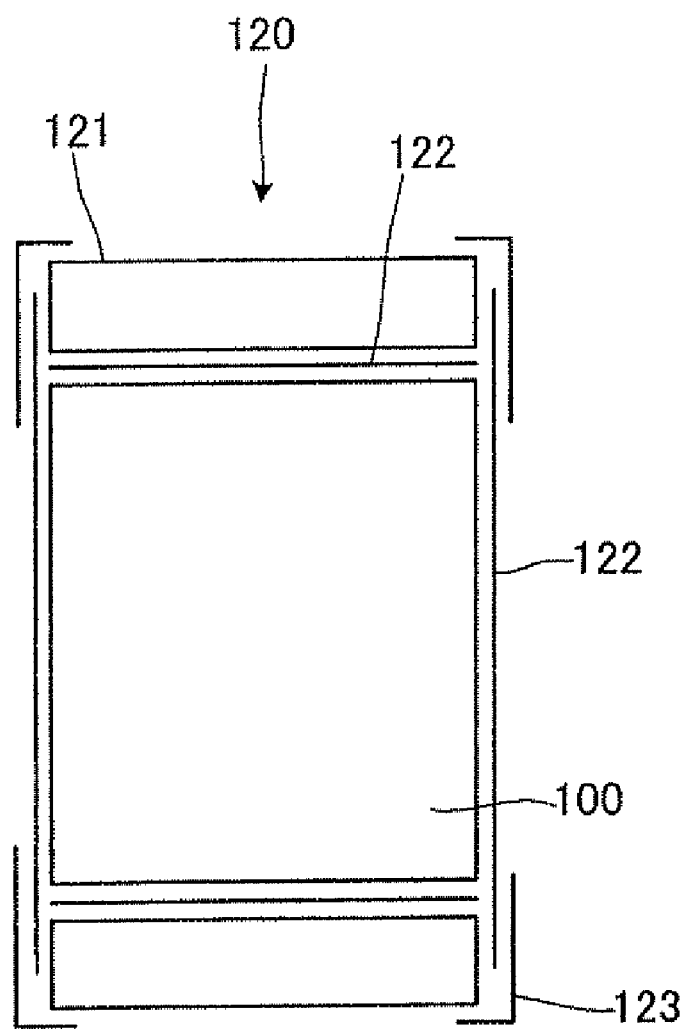
FIG. 12 is a schematic diagram showing the behavior of the honeycomb structure subjected to a treatment for a strength test in the example.

[Strength Test] The honeycomb structure provided with the insertion hole into which the rubber plug was inserted was subjected to an isostatic breakdown strength test. FIG. 11 is a schematic diagram showing a test device, and FIG. 12 is a schematic diagram showing the behavior of the honeycomb structure subjected to a treatment for the strength test. The isostatic breakdown strength test is defined by Automobile Standard JASO Standard M505-87 issued by Society of Automotive Engineers of Japan, and the test was performed in conformity with this standard. Specifically, a honeycomb structure 100 was wrapped in an urethane rubber 122 having a thickness of 0.5 mm, and further an aluminum plate having a thickness of 20 mm was laid and fixed with a vinyl tape 123, thereby obtaining a sample 120 for measuring the strength (see FIG. 12). This sample 120 was introduced in a pressure container 111 filled with water 112, and a valve 114 was closed to increase a pressure in the pressure container 111 to 5 MPa by a pressurizing unit 113 while confirming the pressure with an analog pressure gauge 115 and a digital pressure gauge 116 (see FIG. 11). 5 MPa is a pressure with which a honeycomb structure having the same specifications except that any insertion hole is not provided can bear without being chipped. Afterward, the valve 114 was opened to lower the pressure in the pressure container 111, and the honeycomb structure 1 was taken out to visually observe and evaluate the appearance of the structure. The result of the evaluation is shown in Table 1 together with a drawing number showing the type of the rubber plug, the hardness of the rubber plug, the clearance and the protruding height. It is to be noted that as to the evaluation, a double circle indicates that the structure does not break and that any chip is not generated in an insertion hole portion. A circle indicates that the structure does not break but that slight (allowable) chipping is seen in the insertion hole portion. A cross indicates that the structure is broken.

TABLE 1

|  | Rubber plug type | Rubber plug hardness | Clearance [mm] | Protruding height [mm] | Evaluation |
|---|---|---|---|---|---|
| Comparative Example 1 | FIG. 6 | 45 (65) | 0.2 | 0 | X |
| Example 1 | | | | 0.5 | ○ |
| Example 2 | | | | 3 | ○ |
| Example 3 | | | | 5 | ○ |
| Comparative Example 2 | | | | 6 | X |
| Comparative Example 3 | | | 1.6 | 0 | X |
| Example 4 | | | | 0.5 | ○ |
| Example 5 | | | | 1.5 | ⊙ |
| Example 6 | | | | 3 | ⊙ |
| Example 7 | | | | 5 | ⊙ |
| Comparative Example 4 | | | | 6 | X |
| Comparative Example 5 | | | 2.6 | 0 | X |
| Example 8 | | | | 0.5 | ○ |
| Example 9 | | | | 3 | ○ |
| Example 10 | | | | 5 | ○ |
| Comparative Example 6 | | | | 6 | X |
| Comparative Example 7 | | | 3 | 0.5 | X |
| Comparative Example 8 | | | | 3 | X |
| Comparative Example 9 | | | | 5 | X |

Examples 2 to 20, Comparative Examples 1 to 35, and Reference Examples 1 and 2

The hardness of each rubber plug was changed, and the size of the rubber plug was changed to change a clearance and a protruding height, respectively. Except this respect, in the same manner as in Example 1, each honeycomb structure was prepared and provided with an insertion hole, and the structure including the rubber plug inserted into the hole was subjected to a strength test. The result of evaluation is shown in Tables 1, 2 and 3 together with a drawing number showing the type of the rubber plug, the hardness of the rubber plug, the clearance and the protruding height.

It is to be noted that in Examples 1 to 10 and Comparative Examples 1 to 9, when the rubber plug had a hardness of 65 and the structure had the same conditions other than the hardness, the same result as that in a case where the plug had a hardness of 45 was obtained. Moreover, when the conditions other than the hardness in Examples 11 to 20 and Comparative Examples 27 to 35 were the same and the rubber plug had a hardness of 90, the same result as that in a case where the plug had a hardness of 70 was obtained.

TABLE 2

|  | Rubber plug type | Rubber plug hardness | Clearance [mm] | Protruding height [mm] | Evaluation |
|---|---|---|---|---|---|
| Comparative Example 10 | FIG. 6 | 30 | 0.2 | 0 | X |
| Comparative Example 11 | | | | 0.5 | X |
| Comparative Example 12 | | | | 3 | X |
| Comparative Example 13 | | | | 5 | X |
| Comparative Example 14 | | | | 6 | X |
| Comparative Example 15 | | | 1.6 | 0 | X |
| Comparative Example 16 | | | | 0.5 | X |
| Reference Example 1 | | | | 1.5 | ○ |
| Reference Example 2 | | | | 3 | ○ |
| Comparative Example 17 | | | | 5 | X |
| Comparative Example 18 | | | | 6 | X |
| Comparative Example 19 | | | 2.6 | 0 | X |
| Comparative Example 20 | | | | 0.5 | X |
| Comparative Example 21 | | | | 3 | X |
| Comparative Example 22 | | | | 5 | X |
| Comparative Example 23 | | | | 6 | X |
| Comparative Example 24 | | | 3 | 0.5 | X |
| Comparative Example 25 | | | | 3 | X |
| Comparative Example 26 | | | | 5 | X |

TABLE 3

|  | Rubber plug type | Rubber plug hardness | Clearance [mm] | Protruding height [mm] | Evaluation |
|---|---|---|---|---|---|
| Comparative Example 27 | FIG. 6 | 70 (90) | 0.2 | 0 | X |
| Example 11 | | | | 0.5 | ○ |
| Example 12 | | | | 3 | ○ |
| Example 13 | | | | 5 | ○ |
| Comparative Example 28 | | | | 6 | X |

TABLE 3-continued

|  | Rubber plug type | Rubber plug hardness | Clearance [mm] | Protruding height [mm] | Evaluation |
|---|---|---|---|---|---|
| Comparative Example 29 |  |  | 1.6 | 0 | X |
| Example 14 |  |  |  | 0.5 | ○ |
| Example 15 |  |  |  | 1.5 | ○ |
| Example 16 |  |  |  | 3 | ○ |
| Example 17 |  |  |  | 5 | ○ |
| Comparative Example 30 |  |  |  | 6 | X |
| Comparative Example 31 |  |  | 2.6 | 0 | X |
| Example 18 |  |  |  | 0.5 | ○ |
| Example 19 |  |  |  | 3 | ○ |
| Example 20 |  |  |  | 5 | ○ |
| Comparative Example 32 |  |  |  | 6 | X |
| Comparative Example 33 |  |  | 3 | 0.5 | X |
| Comparative Example 34 |  |  |  | 3 | X |
| Comparative Example 35 |  |  |  | 5 | X |

Example 21

Figure 7:
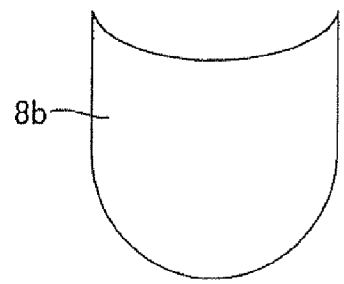
FIG. 7 is a sectional view showing the shape of the rubber plug used in the example and corresponding to the diagram of the insertion hole shown in FIG. 5.

As a rubber plug, a rubber plug having a shape shown in FIG. 7 and a hardness of 70 was used. FIG. 7 is a sectional view showing the shape of a used rubber plug 8b and corresponding to a diagram of the insertion hole 7 shown in FIG. 5. The shape of the used rubber plug 8b was substantially the same as that of the insertion hole 7, so that the only bottom surface thereof was semispherical and another portion was substantially columnar. A top surface portion (an upper surface portion, i.e., an exposed portion of the inserted rubber plug on the side of the peripheral surface of a honeycomb structure) is recessed in a pot-bottom-like shape. Except this respect, in the same manner as in Example 1, the honeycomb structure was prepared and provided with an insertion hole, and the structure including the rubber plug inserted into the hole was subjected to a strength test. The result of evaluation is shown in Table 4 together with a drawing number showing the type of the rubber plug, the hardness of the rubber plug, a clearance and a protruding height.

Examples 22 to 30, and Comparative Examples 36 to 44

The size of each rubber plug was changed to change a clearance and a protruding height, respectively. Except this respect, in the same manner as in Example 21, each honeycomb structure was prepared and provided with an insertion hole, and the structure including the rubber plug inserted into the hole was subjected to a strength test. The result of evaluation is shown in Table 4 together with a drawing number showing the type of the rubber plug, the hardness of the rubber plug, the clearance and the protruding height.

It is to be noted that when conditions other than the hardness were the same in Examples 21 to 30 and Comparative Examples 36 to 44 and the rubber plug had a hardness of 90, the same result as that in a case where the plug had a hardness of 70 was obtained.

TABLE 4

|  | Rubber plug type | Rubber plug hardness | Clearance [mm] | Protruding height [mm] | Evaluation |
|---|---|---|---|---|---|
| Comparative Example 36 | FIG. 7 | 70 (90) | 0.2 | 0 | X |
| Example 21 |  |  |  | 0.5 | ○ |
| Example 22 |  |  |  | 3 | ○ |
| Example 23 |  |  |  | 5 | ○ |
| Comparative Example 37 |  |  |  | 6 | X |
| Comparative Example 38 |  |  | 1.6 | 0 | X |
| Example 24 |  |  |  | 0.5 | ○ |
| Example 25 |  |  |  | 1.5 | ○ |
| Example 26 |  |  |  | 3 | ○ |
| Example 27 |  |  |  | 5 | ○ |
| Comparative Example 39 |  |  |  | 6 | X |
| Comparative Example 40 |  |  | 2.6 | 0 | X |
| Example 28 |  |  |  | 0.5 | ○ |
| Example 29 |  |  |  | 3 | ○ |
| Example 30 |  |  |  | 5 | ○ |
| Comparative Example 41 |  |  |  | 6 | X |
| Comparative Example 42 |  |  | 3 | 0.5 | X |
| Comparative Example 43 |  |  |  | 3 | X |
| Comparative Example 44 |  |  |  | 5 | X |

Example 31

Figure 8:
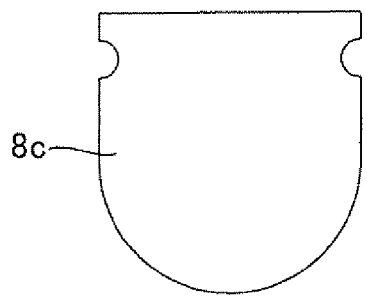
FIG. 8 is a sectional view showing the shape of the rubber plug used in the example and corresponding to the diagram of the insertion hole shown in FIG. 5.

As a rubber plug, a rubber plug having a shape shown in FIG. 8 and a hardness of 70 was used. FIG. 8 is a sectional view showing the shape of a used rubber plug 8c and corresponding to a diagram of the insertion hole 7 shown in FIG. 5. The shape of the used rubber plug 8c was substantially the same as that of the insertion hole 7, so that the only bottom surface thereof was semispherical and another portion was substantially columnar. However, a columnar portion (a portion facing the inner surface of the insertion hole 7) has a recessed portion. Since FIG. 8 shows a section, it does not clearly show the recessed portion, but the portion is circumferentially formed around the columnar portion. Except this respect, in the same manner as in Example 1, a honeycomb structure was prepared and provided with an insertion hole, and the structure including the rubber plug inserted into the hole was subjected to a strength test. The result of evaluation is shown in Table 5 together with a drawing number showing the type of the rubber plug, the hardness of the rubber plug, a clearance and a protruding height.

Examples 32 to 40, and Comparative Examples 45 to 53

The size of each rubber plug was changed to change a clearance and a protruding height, respectively. Except this respect, in the same manner as in Example 31, each honeycomb structure was prepared and provided with an insertion hole, and the structure including the rubber plug inserted into the hole was subjected to a strength test. The result of evaluation is shown in Table 5 together with a drawing number showing the type of the rubber plug, the hardness of the rubber plug, the clearance and the protruding height.

It is to be noted that when conditions other than the hardness in Examples 31 to 40 and Comparative Examples 45 to 53 were the same and the rubber plug had a hardness of 90, the same result as that in a case where the plug had a hardness of 70 was obtained.

Example 41

Figure 9:
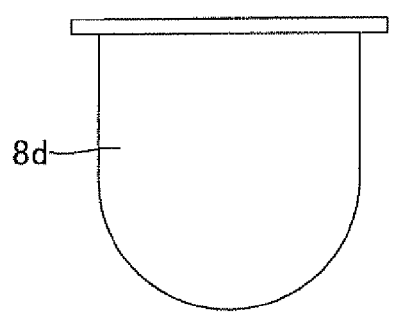
FIG. 9 is a sectional view showing the shape of the rubber plug used in the example and corresponding to the diagram of the insertion hole shown in FIG. 5.

As a rubber plug, a rubber plug having a shape shown in FIG. 9 and a hardness of 70 was used. FIG. 9 is a sectional view showing the shape of a used rubber plug 8d and corresponding to a diagram of the insertion hole 7 shown in FIG. 5. The shape of the used rubber plug 8d was substantially the same as that of the insertion hole 7, so that the only bottom surface thereof was semispherical and another portion was substantially columnar. However, the diameter of an only top surface portion was increased to form a window-roof-like portion. Except this respect, in the same manner as in Example 1, a honeycomb structure was prepared and provided with an insertion hole, and the structure including the rubber plug inserted into the hole was subjected to a strength test. The result of evaluation is shown in Table 6 together with a drawing number showing the type of the rubber plug, the hardness of the rubber plug, a clearance and a protruding height.

Examples 42 to 50, and Comparative Examples 54 to 62

The size of each rubber plug was changed to change a clearance and a protruding height, respectively. Except this respect, in the same manner as in Example 41, each honeycomb structure was prepared and provided with an insertion hole, and the structure including the rubber plug inserted into the hole was subjected to a strength test. The result of evaluation is shown in Table 6 together with a drawing number showing the type of the rubber plug, the hardness of the rubber plug, the clearance and the protruding height.

It is to be noted that when conditions other than the hardness were the same in Examples 41 to 50 and Comparative Examples 54 to 62 and the rubber plug had a hardness of 90, the same result as that in a case where the plug had a hardness of 70 was obtained.

TABLE 5

| | Rubber plug type | Rubber plug hardness | Clearance [mm] | Protruding height [mm] | Evaluation |
|---|---|---|---|---|---|
| Comparative Example 45 | FIG. 8 | 70 (90) | 0.2 | 0 | X |
| Example 31 | | | | 0.5 | ⊚ |
| Example 32 | | | | 3 | ⊚ |
| Example 33 | | | | 5 | ⊚ |
| Comparative Example 46 | | | | 6 | X |
| Comparative Example 47 | | | 1.6 | 0 | X |
| Example 34 | | | | 0.5 | ⊚ |
| Example 35 | | | | 1.5 | ⊚ |
| Example 36 | | | | 3 | ⊚ |
| Example 37 | | | | 5 | ⊚ |
| Comparative Example 48 | | | | 6 | X |
| Comparative Example 49 | | | 2.6 | 0 | X |
| Example 38 | | | | 0.5 | ⊚ |
| Example 39 | | | | 3 | ⊚ |
| Example 40 | | | | 5 | ⊚ |
| Comparative Example 50 | | | | 6 | X |
| Comparative Example 51 | | | 3 | 0.5 | X |
| Comparative Example 52 | | | | 3 | X |
| Comparative Example 53 | | | | 5 | X |

TABLE 6

|  | Rubber plug type | Rubber plug hardness | Clearance [mm] | Protruding height [mm] | Evaluation |
|---|---|---|---|---|---|
| Comparative Example 54 | FIG. 9 | 70 (90) | 0.2 | 0 | X |
| Example 41 |  |  |  | 0.5 | ○ |
| Example 42 |  |  |  | 3 | ○ |
| Example 43 |  |  |  | 5 | ○ |
| Comparative Example 55 |  |  |  | 6 | X |
| Comparative Example 56 |  |  | 1.6 | 0 | X |
| Example 44 |  |  |  | 0.5 | ○ |
| Example 45 |  |  |  | 1.5 | ○ |
| Example 46 |  |  |  | 3 | ○ |
| Example 47 |  |  |  | 5 | ○ |
| Comparative Example 57 |  |  |  | 6 | X |
| Comparative Example 58 |  |  | 2.6 | 0 | X |
| Example 48 |  |  |  | 0.5 | ○ |
| Example 49 |  |  |  | 3 | ○ |
| Example 50 |  |  |  | 5 | ○ |
| Comparative Example 59 |  |  |  | 6 | X |
| Comparative Example 60 |  |  | 3 | 0.5 | X |
| Comparative Example 61 |  |  |  | 3 | X |
| Comparative Example 62 |  |  |  | 5 | X |

Example 51

There was prepared a honeycomb structure of an elliptic post shape including an elliptic section vertical to a central axis, the elliptic section having a 131 mm major axis and a 86 mm minor axis (see the shape shown in FIGS. 3A and 3B). Cells had thicknesses of 4 mil, a cell density was 600 cells/square inch, and the other specifications were the same as those of the honeycomb structure prepared in Example 1. Then, in the center of the peripheral surface of the resultant honeycomb structure, an insertion hole was obliquely formed toward the central axis at an ellipse major axis position in the section vertical to the central axis and with an angle of 10° with respect to the section vertical to the central axis (with an angle of 10° with respect to an end face) (see the configuration shown by the insertion hole 7b of FIG. 3A and the insertion hole 7d of FIG. 3B). The insertion hole (a space) had the same shape as that of Example 1 (see FIG. 5) except that the hole was obliquely formed. Moreover, as a rubber plug to be inserted into the insertion hole, there was used a rubber plug formed based on the shape shown in FIG. 6 so that the rubber plug had a uniform protruding height and so that a top surface portion of the columnar plug was obliquely formed in accordance with the oblique insertion hole. The rubber plug had a hardness of 70. Except these respects, in the same manner as in Example 1, the honeycomb structure was prepared and provided with the insertion hole, and the structure including the rubber plug inserted into the hole was subjected to a strength test. The result of evaluation is shown in Table 7 together with a drawing number showing the type of the rubber plug, the hardness of the rubber plug, a clearance and a protruding height.

Examples 52 to 60, and Comparative Examples 63 to 71

The size of each rubber plug was changed to change a clearance and a protruding height, respectively. Except this respect, in the same manner as in Example 51, each honeycomb structure was prepared and provided with an insertion hole, and the structure including the rubber plug inserted into the hole was subjected to a strength test. The result of evaluation is shown in Table 7 together with a drawing number showing the type of the rubber plug, the hardness of the rubber plug, the clearance and the protruding height.

It is to be noted that when conditions other than the hardness in Examples 51 to 60 and Comparative Examples 63 to 71 were the same and the rubber plug had a hardness of 90, the same result as that in a case where the plug had a hardness of 70 was obtained. Moreover, in a case where conditions other than the angle of an insertion hole with respect to a section vertical to a central axis in Examples 51 to 60 and Comparative Examples 63 to 71 were the same and in the center of the peripheral surface of each honeycomb structure, an insertion hole was obliquely formed toward the central axis at an ellipse major axis position in the section vertical to the central axis and with an angle of 20° with respect to the section vertical to the central axis (with an angle of 20° with respect to an end face) (see the configuration shown by the insertion hole 7b of FIG. 3A and the insertion hole 7d of FIG. 3B (the angle with respect to the end face varied)), the same result as that in Examples 51 to 60 and Comparative Examples 63 to 71 was obtained. Furthermore, in a case where conditions other than the angle of the insertion hole with respect to the section vertical to the central axis in Examples 51 to 60 and Comparative Examples 63 to 71 were the same and in the center of the peripheral surface of the honeycomb structure, the insertion hole was formed toward the central axis at the ellipse major axis position in the section vertical to the central axis and in parallel with the section vertical to the central axis (in parallel with the end face) (see the configuration shown by the insertion hole 7b of FIG. 3A and the insertion hole 7c of FIG. 3B), the same result as that in Examples 51 to 60 and Comparative Examples 63 to 71 was obtained.

TABLE 7

| | Rubber plug type | Rubber plug hardness | Clearance [mm] | Protruding height [mm] | Evaluation |
|---|---|---|---|---|---|
| Comparative Example 63 | FIG. 6 | 70 (90) | 0.2 | 0 | X |
| Example 51 | | | | 0.5 | ○ |
| Example 52 | | | | 3 | ○ |
| Example 53 | | | | 5 | ○ |
| Comparative Example 64 | | | | 6 | X |
| Comparative Example 65 | | | 1.6 | 0 | X |
| Example 54 | | | | 0.5 | ○ |
| Example 55 | | | | 1.5 | ○ |
| Example 56 | | | | 3 | ○ |
| Example 57 | | | | 5 | ○ |
| Comparative Example 66 | | | | 6 | X |
| Comparative Example 67 | | | 2.6 | 0 | X |
| Example 58 | | | | 0.5 | ○ |
| Example 59 | | | | 3 | ○ |
| Example 60 | | | | 5 | ○ |
| Comparative Example 68 | | | | 6 | X |
| Comparative Example 69 | | | 3 | 0.5 | X |
| Comparative Example 70 | | | | 3 | X |
| Comparative Example 71 | | | | 5 | X |

Example 61

As a rubber plug, there was used a rubber plug formed based on the shape shown in FIG. 8 so that the rubber plug had a uniform protruding height and so that a top surface portion of the columnar plug was obliquely formed in accordance with an oblique insertion hole. Except this respect, in the same manner as in Example 51, a honeycomb structure was prepared and provided with the insertion hole, and the structure including the rubber plug inserted into the hole was subjected to a strength test. The result of evaluation is shown in Table 8 together with a drawing number showing the type of the rubber plug, the hardness of the rubber plug, a clearance and a protruding height. It is to be noted that since the insertion hole was obliquely formed, to use the rubber plug having the obliquely formed top surface portion of the columnar article in accordance with the insertion hole, a rubber plug was circumferentially formed around the columnar portion of the rubber plug in a position where a distance between the inserted plug and the peripheral surface of the honeycomb structure was uniform.

Examples 62 to 70, and Comparative Examples 72 to 80

The size of each rubber plug was changed to change a clearance and a protruding height, respectively. Except this respect, in the same manner as in Example 61, each honeycomb structure was prepared and provided with an insertion hole, and the structure including the rubber plug inserted into the hole was subjected to a strength test. The result of evaluation is shown in Table 8 together with a drawing number showing the type of the rubber plug, the hardness of the rubber plug, the clearance and the protruding height.

It is to be noted that when conditions other than the hardness in Examples 61 to 70 and Comparative Examples 72 to 80 were the same and the rubber plug had a hardness of 90, the same result as that in a case where the plug had a hardness of 70 was obtained. Moreover, in Examples 61 to 70 and Comparative Examples 72 to 80, in the same manner as in Example 51, in the center of the peripheral surface of each resultant honeycomb structure, an insertion hole was obliquely formed toward a central axis at an ellipse major axis position in a section vertical to the central axis and with an angle of 10° with respect to the section vertical to the central axis (with an angle of 10° with respect to an end face) (see the configuration shown by the insertion hole 7b of FIG. 3A and the insertion hole 7d of FIG. 3B). However, in a case where conditions other than the angle of the insertion hole with respect to the section vertical to the central axis in Examples 61 to 70 and Comparative Examples 72 to 80 were the same and in the center of the peripheral surface of the honeycomb structure, the insertion hole was formed toward the central axis at the ellipse major axis position in the section vertical to the central axis and with an angle of 20° with respect to the section vertical to the central axis (with an angle of 20° with respect to the end face) (see the configuration shown by the insertion hole 7b of FIG. 3A and the insertion hole 7d of FIG. 3B (the angle with respect to the end face varied), the same result as that in Examples 61 to 70 and Comparative Examples 72 to 80 was obtained. Furthermore, in a case where conditions other than the angle of the insertion hole with respect to the section vertical to the central axis in Examples 61 to 70 and Comparative Examples 72 to 80 were the same and in the center of the peripheral surface of the honeycomb structure, the insertion hole was formed toward the central axis at the ellipse major axis position in the section vertical to the central axis and in parallel with the section vertical to the central axis (in parallel with the end face) (see the configuration shown by the insertion hole 7b of FIG. 3A and the insertion hole 7c of FIG. 3B), the same result as that in Examples 61 to 70 and Comparative Examples 72 to 80 was obtained.

TABLE 8

|  | Rubber plug type | Rubber plug hardness | Clearance [mm] | Protruding height [mm] | Evaluation |
|---|---|---|---|---|---|
| Comparative Example 72 | FIG. 8 | 70 (90) | 0.2 | 0 | X |
| Example 61 |  |  |  | 0.5 | ◎ |
| Example 62 |  |  |  | 3 | ◎ |
| Example 63 |  |  |  | 5 | ◎ |
| Comparative Example 73 |  |  |  | 6 | X |
| Comparative Example 74 |  |  | 1.6 | 0 | X |
| Example 64 |  |  |  | 0.5 | ◎ |
| Example 65 |  |  |  | 1.5 | ◎ |
| Example 66 |  |  |  | 3 | ◎ |
| Example 67 |  |  |  | 5 | ◎ |
| Comparative Example 75 |  |  |  | 6 | X |
| Comparative Example 76 |  |  | 2.6 | 0 | X |
| Example 68 |  |  |  | 0.5 | ◎ |
| Example 69 |  |  |  | 3 | ◎ |
| Example 70 |  |  |  | 5 | ◎ |
| Comparative Example 77 |  |  |  | 6 | X |
| Comparative Example 78 |  |  | 3 | 0.5 | X |
| Comparative Example 79 |  |  |  | 3 | X |
| Comparative Example 80 |  |  |  | 5 | X |

Example 71

In the center of the peripheral surface of a honeycomb structure, an insertion hole was obliquely formed toward a central axis at a position of 45° from a major axis (similarly from a minor axis) at a time when a coordinate axis was constituted of the major and minor axes of an ellipse in a section vertical to the central axis, and with an angle of 10° with respect to the section vertical to the central axis (with an angle of 10° with respect to an end face) (see the configuration shown by the insertion hole 7f of FIG. 3A and the insertion hole 7d of FIG. 3B). Except this respect, in the same manner as in Example 51, the honeycomb structure was prepared and provided with the insertion hole, and the structure including the rubber plug inserted into the hole was subjected to a strength test. The result of evaluation is shown in Table 9 together with a drawing number showing the type of the rubber plug, the hardness of the rubber plug, a clearance and a protruding height.

Examples 72 to 80, and Comparative Examples 81 to 89

The size of each rubber plug was changed to change a clearance and a protruding height, respectively. Except this respect, in the same manner as in Example 71, each honeycomb structure was prepared and provided with an insertion hole, and the structure including the rubber plug inserted into the hole was subjected to a strength test. The result of evaluation is shown in Table 9 together with a drawing number showing the type of the rubber plug, the hardness of the rubber plug, the clearance and the protruding height.

It is to be noted that when conditions other than the hardness in Examples 71 to 80 and Comparative Examples 81 to 89 were the same and the rubber plug had a hardness of 90, the same result as that in a case where the plug had a hardness of 70 was obtained. Moreover, in a case where conditions other than the angle of an insertion hole with respect to a section vertical to a central axis in Examples 71 to 80 and Comparative Examples 81 to 89 were the same and in the center of the peripheral surface of each honeycomb structure, an insertion hole was obliquely formed toward the central axis at a position of 45° from a major axis (similarly from a minor axis) at a time when a coordinate axis was constituted of the major and minor axes of an ellipse in the section vertical to the central axis, and with an angle of 20° with respect to the section vertical to the central axis (with an angle of 20° with respect to an end face) (see the configuration shown by the insertion hole 7f of FIG. 3A and the insertion hole 7d of FIG. 3B (the angle with respect to the end face varied)), the same result as that in Examples 71 to 80 and Comparative Examples 81 to 89 was obtained. Furthermore, in a case where conditions other than the angle of the insertion hole with respect to the section vertical to the central axis in Examples 71 to 80 and Comparative Examples 81 to 89 were the same and in the center of the peripheral surface of the honeycomb structure, the insertion hole was formed toward the central axis at a position of 45° from the major axis (similarly from the minor axis) at a time when the coordinate axis was constituted of the major and minor axes of the ellipse in the section vertical to the central axis, and in parallel with the section vertical to the central axis (in parallel with the end face) (see the configuration shown by the insertion hole 7f of FIG. 3A and the insertion hole 7c of FIG. 3B), the same result as that in Examples 71 to 80 and Comparative Examples 81 to 89 was obtained.

TABLE 9

|  | Rubber plug type | Rubber plug hardness | Clearance [mm] | Protruding height [mm] | Evaluation |
|---|---|---|---|---|---|
| Comparative Example 81 | FIG. 6 | 70 (90) | 0.2 | 0 | X |
| Example 71 |  |  |  | 0.5 | ○ |

TABLE 9-continued

| | Rubber plug type | Rubber plug hardness | Clearance [mm] | Protruding height [mm] | Evaluation |
|---|---|---|---|---|---|
| Example 72 | | | | 3 | ○ |
| Example 73 | | | | 5 | ○ |
| Comparative Example 82 | | | | 6 | X |
| Comparative Example 83 | | | 1.6 | 0 | X |
| Example 74 | | | | 0.5 | ○ |
| Example 75 | | | | 1.5 | ○ |
| Example 76 | | | | 3 | ○ |
| Example 77 | | | | 5 | ○ |
| Comparative Example 84 | | | | 6 | X |
| Comparative Example 85 | | | 2.6 | 0 | X |
| Example 78 | | | | 0.5 | ○ |
| Example 79 | | | | 3 | ○ |
| Example 80 | | | | 5 | ○ |
| Comparative Example 86 | | | | 6 | X |
| Comparative Example 87 | | | 3 | 0.5 | X |
| Comparative Example 88 | | | | 3 | X |
| Comparative Example 89 | | | | 5 | X |

Example 81

In the center of the peripheral surface of a honeycomb structure, an insertion hole was obliquely formed toward a central axis at an ellipse minor axis position in a section vertical to the central axis and with an angle of 10° with respect to the section vertical to the central axis (with an angle of 10° with respect to an end face) (see the configuration shown by the insertion hole 7e of FIG. 3A and the insertion hole 7d of FIG. 3B). Except this respect, in the same manner as in Example 51, the honeycomb structure was prepared and provided with the insertion hole, and the structure including a rubber plug inserted into the hole was subjected to a strength test. The result of evaluation is shown in Table 10 together with a drawing number showing the type of the rubber plug, the hardness of the rubber plug, a clearance and a protruding height.

Examples 82 to 90, and Comparative Examples 90 to 98

The size of each rubber plug was changed to change a clearance and a protruding height, respectively. Except this respect, in the same manner as in Example 81, each honeycomb structure was prepared and provided with an insertion hole, and the structure including the rubber plug inserted into the hole was subjected to a strength test. The result of evaluation is shown in Table 10 together with a drawing number showing the type of the rubber plug, the hardness of the rubber plug, the clearance and the protruding height.

It is to be noted that when conditions other than the hardness in Examples 81 to 90 and Comparative Examples 90 to 98 were the same and the rubber plug had a hardness of 90, the same result as that in a case where the plug had a hardness of 70 was obtained. Moreover, in a case where conditions other than the angle of the insertion hole with respect to a section vertical to a central axis in Examples 81 to 90 and Comparative Examples 90 to 98 were the same and in the center of the peripheral surface of each honeycomb structure, an insertion hole was obliquely formed toward the central axis at an ellipse minor axis position in the section vertical to the central axis and with an angle of 20° with respect to the section vertical to the central axis (with an angle of 20° with respect to an end face) (see the configuration shown by the insertion hole 7e of FIG. 3A and the insertion hole 7d of FIG. 3B (the angle with respect to the end face varied)), the same result as that in Examples 81 to 90 and Comparative Examples 90 to 98 was obtained. Furthermore, in a case where conditions other than the angle of the insertion hole with respect to the section vertical to the central axis in Examples 81 to 90 and Comparative Examples 90 to 98 were the same and in the center of the peripheral surface of the honeycomb structure, the insertion hole was formed toward the central axis at the ellipse minor axis position in the section vertical to the central axis and in parallel with the section vertical to the central axis (in parallel with the end face) (see the configuration shown by the insertion hole 7e of FIG. 3A and the insertion hole 7c of FIG. 3B), the same result as that in Examples 81 to 90 and Comparative Examples 90 to 98 was obtained.

TABLE 10

| | Rubber plug type | Rubber plug hardness | Clearance [mm] | Protruding height [mm] | Evaluation |
|---|---|---|---|---|---|
| Comparative Example 90 | FIG. 6 | 70 (90) | 0.2 | 0 | X |
| Example 81 | | | | 0.5 | ○ |
| Example 82 | | | | 3 | ○ |
| Example 83 | | | | 5 | ○ |
| Comparative Example 91 | | | | 6 | X |
| Comparative Example 92 | | | 1.6 | 0 | X |
| Example 84 | | | | 0.5 | ○ |
| Example 85 | | | | 1.5 | ○ |
| Example 86 | | | | 3 | ○ |
| Example 87 | | | | 5 | ○ |

TABLE 10-continued

|  | Rubber plug type | Rubber plug hardness | Clearance [mm] | Protruding height [mm] | Evaluation |
|---|---|---|---|---|---|
| Comparative Example 93 |  |  |  | 6 | X |
| Comparative Example 94 |  |  | 2.6 | 0 | X |
| Example 88 |  |  |  | 0.5 | ○ |
| Example 89 |  |  |  | 3 | ○ |
| Example 90 |  |  |  | 5 | ○ |
| Comparative Example 95 |  |  |  | 6 | X |
| Comparative Example 96 |  |  | 3 | 0.5 | X |
| Comparative Example 97 |  |  |  | 3 | X |
| Comparative Example 98 |  |  |  | 5 | X |

Comparative Example 99

Instead of inserting a rubber plug into an insertion hole, a circular stainless steel plate formed into a curved-face-like shape in accordance with the peripheral surface of a honeycomb structure and having a diameter of 45 mm and a thickness of 0.8 mm was bonded so as to close the insertion hole. Except these respects, in the same manner as in Example 1, the honeycomb structure was prepared and provided with the insertion hole, and the structure including the insertion hole closed with the stainless steel plate was subjected to a strength test. The result of evaluation was a cross. It is to be noted that in a case where a large stainless steel plate having a diameter of 80 mm was used and conditions other than the size of the stainless steel plate were the same, the same result as that in a case where the stainless steel plate having a diameter of 45 mm was used was obtained. Moreover, in a case where thick stainless steel plates having thicknesses of 1.0 mm, 1.2 mm, 1.5 mm and 2.0 mm, respectively, were used and conditions other than the thickness of the stainless steel plate were the same, the same result as that in a case where the stainless steel plate having a thickness of 0.8 mm was used was obtained.

Comparative Example 100

Instead of inserting a rubber plug into an insertion hole, a circular stainless steel plate formed into a curved-face-like shape in accordance with the peripheral surface of a honeycomb structure and having a diameter of 45 mm and a thickness of 0.8 mm was bonded so as to close the insertion hole while an urethane sheet having a size equal to that of the stainless steel plate was interposed between the stainless steel plate and the insertion hole (the peripheral surface). Except these respects, in the same manner as in Example 1, the honeycomb structure was prepared and provided with the insertion hole, and the structure including the insertion hole closed with the stainless steel plate and the urethane sheet was subjected to a strength test. The result of evaluation was a cross. It is to be noted that in a case where a large stainless steel plate having a diameter of 80 mm and the corresponding urethane sheet were used and conditions other than the sizes of the stainless steel plate and the urethane sheet were the same, the same result as that in a case where the stainless steel plate having a diameter of 45 mm and the corresponding urethane sheet were used was obtained. Moreover, in a case where thick stainless steel plates having thicknesses of 1.0 mm, 1.2 mm, 1.5 mm and 2.0 mm, respectively, were used and conditions other than the thickness of the stainless steel plate were the same, the same result as that in a case where the stainless steel plate having a thickness of 0.8 mm was used was obtained.

Comparative Example 101

Figure 10:
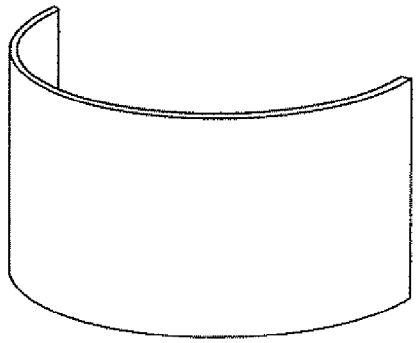
FIG. 10 is a perspective view showing the shape of a stainless steel plate used in the example.

Instead of inserting a rubber plug into an insertion hole, a rectangular stainless steel plate formed into a curved-face-like shape in accordance with the peripheral surface of a honeycomb structure and having a vertical size of 60 mm, a horizontal size of 150 mm and a thickness of 1.2 mm was bonded so as to close the insertion hole. FIG. 10 is a perspective view showing the shape of the used stainless steel plate and a use configuration thereof. Except these respects, in the same manner as in Example 1, the honeycomb structure was prepared and provided with the insertion hole, and the structure including the insertion hole closed with the stainless steel plate was subjected to a strength test. The result of evaluation was a cross. It is to be noted that in a case where a thick stainless steel plate having a thickness of 1.5 mm or 2.0 mm was used and conditions other than the thickness of the stainless steel plate were the same, the same result as that in a case where the stainless steel plate having a thickness of 1.2 mm was used was obtained.

Comparative Example 102

Instead of inserting a rubber plug into an insertion hole, a rectangular stainless steel plate formed into a curved-face-like shape in accordance with the peripheral surface of a honeycomb structure and having a vertical size of 60 mm, a lateral size of 150 mm and a thickness of 1.2 mm was bonded so as to close the insertion hole while an urethane sheet having a size equal to that of the stainless steel plate was interposed between the stainless steel plate and the insertion hole (the peripheral surface). FIG. 10 is a perspective view showing the shape of the used stainless steel plate and a use configuration thereof. Except these respects, in the same manner as in Example 1, the honeycomb structure was prepared and provided with the insertion hole, and the structure including the insertion hole closed with the stainless steel plate and the urethane sheet was subjected to a strength test. The result of evaluation was a cross. It is to be noted that in a case where a thick stainless steel plate having a thickness of 1.5 mm or 2.0 mm was used and conditions other than the thickness of the stainless steel plate were the same, the same result as that in a case where the stainless steel plate having a thickness of 1.2 mm was used was obtained.

Comparative Example 103

Instead of inserting a rubber plug into an insertion hole, the insertion hole was filled with a hot bond made of an ethylene-vinyl acetate copolymer resin, followed by solidifying the bond. Except these respects, in the same manner as in Example 1, a honeycomb structure was prepared and provided with the insertion hole, and the structure including the insertion hole filled with the hot bond was subjected to a strength test. The result of evaluation was a cross.

Comparative Example 104

Instead of inserting a rubber plug into an insertion hole, the insertion hole was filled with a ceramic adhesive made of alumina as a main material, followed by solidifying the adhesive. Except these respects, in the same manner as in Example 1, a honeycomb structure was prepared and provided with the insertion hole, and the structure including the insertion hole filled with the ceramic adhesive was subjected to a strength test. The result of evaluation was a cross.

A strength measuring method of a honeycomb structure according to the present invention is preferably used as means for measuring the strength of the honeycomb structure having the outer surface thereof provided with an insertion hole. Examples of such a honeycomb structure include a honeycomb structure to which a sensor such as an oxygen sensor is attached and which is used in, for example, an exhaust system of any type of internal combustion engine, to monitor the function of a catalyst converter.

What is claimed is:

1. A strength measuring method of a honeycomb structure provided with an insertion hole, in which the strength of the honeycomb structure is measured while a rubber plug satisfying the following conditions (1) to (3) is inserted into the insertion hole:
   (1) the rubber plug has a hardness of 45 or more and 90 or less;
   (2) a clearance between the inserted rubber plug and the inner surface of the insertion hole parallel to the depth direction of the insertion hole is 0.2 mm or more and 2.6 mm or less; and
   (3) the protruding height of the inserted rubber plug from the outer surface of the honeycomb structure is 0.5 mm or more and 5 mm or less.

2. The strength measuring method of the honeycomb structure according to claim 1, wherein the rubber plug further satisfies the following condition (4):
   (4) the rubber plug has a recessed portion in the face thereof facing the inner surface of the insertion hole.

3. The strength measuring method of the honeycomb structure according to claim 2, wherein the bottom of the insertion hole has a semispherical shape.

4. The strength measuring method of the honeycomb structure according to claim 3, wherein the strength is measured by an isostatic breakdown strength test defined by Automobile Standard JASO Standard M505-87 issued by Society of Automotive Engineers of Japan.

5. The strength measuring method of the honeycomb structure according to claim 2, wherein the strength is measured by an isostatic breakdown strength test defined by Automobile Standard JASO Standard M505-87 issued by Society of Automotive Engineers of Japan.

6. The strength measuring method of the honeycomb structure according to claim 1, wherein the bottom of the insertion hole has a semispherical shape.

7. The strength measuring method of the honeycomb structure according to claim 6, wherein the strength is measured by an isostatic breakdown strength test defined by Automobile Standard JASO Standard M505-87 issued by Society of Automotive Engineers of Japan.

8. The strength measuring method of the honeycomb structure according to claim 1, wherein the honeycomb structure has the shape of a straight post including a circular or elliptic section vertical to a central axis, and the peripheral surface of the honeycomb structure having the straight post shape is provided with the insertion hole.

9. The strength measuring method of the honeycomb structure according to claim 8, wherein the rubber plug further satisfies the following condition (4):
   (4) the rubber plug has a recessed portion in the face thereof facing the inner surface of the insertion hole.

10. The strength measuring method of the honeycomb structure according to claim 9, wherein the bottom of the insertion hole has a semispherical shape.

11. The strength measuring method of the honeycomb structure according to claim 10, wherein the strength is measured by an isostatic breakdown strength test defined by Automobile Standard JASO Standard M505-87 issued by Society of Automotive Engineers of Japan.

12. The strength measuring method of the honeycomb structure according to claim 9, wherein the strength is measured by an isostatic breakdown strength test defined by Automobile Standard JASO Standard M505-87 issued by Society of Automotive Engineers of Japan.

13. The strength measuring method of the honeycomb structure according to claim 8, wherein the bottom of the insertion hole has a semispherical shape.

14. The strength measuring method of the honeycomb structure according to claim 13, wherein the strength is measured by an isostatic breakdown strength test defined by Automobile Standard JASO Standard M505-87 issued by Society of Automotive Engineers of Japan.

15. The strength measuring method of the honeycomb structure according to claim 8, wherein the strength is measured by an isostatic breakdown strength test defined by Automobile Standard JASO Standard M505-87 issued by Society of Automotive Engineers of Japan.

16. The strength measuring method of the honeycomb structure according to claim 1, wherein the strength is measured by an isostatic breakdown strength test defined by Automobile Standard JASO Standard M505-87 issued by Society of Automotive Engineers of Japan.

* * * * *